United States Patent [19]

Kirsch

[11] Plant 4,605

[45] Oct. 28, 1980

[54] LILY PLANT NAMED STAR DUSTER

[75] Inventor: Ted T. Kirsch, Myrtle Point, Oreg.

[73] Assignee: Sun Valley Bulb Farms, Inc., Myrtle Point, Oreg.

[21] Appl. No.: 62,315

[22] Filed: Jul. 30, 1979

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new variety of Asiatic hybrid lily plant of the chalice type distinguished by its short and stocky growth habit and by the brilliant, prominently spotted, orange-red coloring of its medium sized, five to six inch diameter, slightly cupped flowers borne with strong, upright pedicels carried raceme on a short, strong stem; each pedicel having one or two buds or flowers.

2 Drawing Figures

BACKGROUND OF THE NEW PLANT

My new lily plant was discovered by me as a seedling of unknown parentage growing at my nursery in Arcata, Calif. Its short and stocky growth habit and the brilliant coloring of its upright flowers attracted me to propagate this new plant by scales to test its habits, with the result that I have found the plant to have advantageous and distinctive characteristics which made me believe it would have considerable value for commercial lily plant culture. I carried on further propagation of this new lily plant through successive generations by means of scales, as well as by tissue culture, at Arcata, Calif., and I have found that the distinctive characteristics of this plant hold true from generation to generation and appear to be firmly fixed.

DESCRIPTION OF THE DRAWING

My new variety of lily plant is illustrated by the accompanying full color photographic drawing which in the upper view shows a blooming pot plant arising from a rather small bulb, and in the lower view a close-up of the fully opened flower. The color rendition in this drawing is as nearly true as can be reasonably obtained by conventional photographic procedures.

DESCRIPTION OF THE NEW PLANT

The following is a detailed description of my new variety of lily plant as observed at Arcata, Calif., with color designations according to The R.H.S. Colour Chart prepared by The Royal Horticultural Society of London, England, with collaboration by the British Colour Council.

THE PLANT

Origin: Seedling.
Parentage: Unknown.
Classification:
*Botanic.*—Asiatic hybrid, chalice-type.
*Commercial.*—Lily plant for pot plant culture.
Form: Tall, single stem arising from each bulb.
Height: About $1\frac{1}{2}$ to 2 feet tall, depending upon the size or age of the bulb.
Growth: Sturdy and upright with excellent strength.
Stem size: From $\frac{1}{4}$ inch in diameter near base when the plant is about 1 foot high to about $\frac{1}{2}$ inch in diameter in plants reaching a height of 2 feet.

*Color.*—Dark maroon, speckled with green.
Foliage: Quantity — abundant.
*Size of leaf.*—Stem leaves are from 2 to 4 inches long and from about $\frac{1}{8}$ to $\frac{1}{4}$ inch wide; and the leaves at the flower cluster are 3 in number, about $1\frac{3}{4}$ to $2\frac{1}{2}$ inches long and about $\frac{1}{4}$ to $\frac{1}{2}$ inch wide.
*Shape of leaf.*—Linear.
*Texture.*—Leathery.
*Aspect.*—Slightly pubescent with hairs about 1/16 inch long on the edge of the leaf.
*Color.*—Upper side — dark green. Under side — light green.
Stem bulblets (under ground):
*Occurrence.*—4 to 12 on each healthy, normal plant at digging time.
*Size.*—About $\frac{1}{4}$ to 1 inch in diameter.
*Color.*—White.
Bulbs:
*Size.*—From about 1 to 3 inches in diameter.
*Color.*—White.

THE BUD

Form: Elongate-oblong with a retuse apex.
Size: From about 2 to 3 inches long and $\frac{1}{2}$ to $\frac{3}{4}$ inch in diameter.
Opening rate: Normal, with tertiary and secondary buds opening successively.
Color: When sepals first divide and petals begin to unfurl, the color is a reddish-orange with green tint.
Surface texture: Pubescent with white hairs about 1/16 inch long.
Pedicel: Strong and generally upright and angled about 30° from the vertical.
*Length.*—$\frac{1}{2}$ to 2 inches.
*Color.*—Dark maroon speckled with green.
*Number of buds.*—Usually one, occasionally two on each pedicel.

THE FLOWER

Blooming habit: Annually, blooming profusely in June.
Size of flower: Medium, averaging about 5 to 6 inches in diameter and about $\frac{3}{4}$ inch in depth.
Borne: From large bulbs, the inflorescence is raceme for the first 2 to 6 pedicels, generally each pedicel with only 1 bud and then, at the top, the stem breaks into an umbel cluster of 2 or 3 pedicels with 1 bloom on each pedicel. Small bulbs often produce an umbel cluster with 1 bloom on each pedicel. The size of the bulb and its cultural care will determine the number of blooms and buds to be found with any given inflorescence. From large bulbs, this plant may have from 6 to 8 blooms open at one time, 1 bloom on each pedicel and 1 or 2 blooms open in the top umbel cluster.

Shape: Slightly cupped with uniformly spaced petals in star arrangement, with the tips of the petals folding slightly and curving backwardly.

Petalage: Normal, 3 sepals and 3 petals.

*Form.*—Oval, with an acute apex, a prominent nectariferous groove, and a center furrow bisecting each petal longitudinally. The petals are about 1 to 2 inches in width and the edges are entire.

*Color.*—Upper side — upon opening, the petals have a background color RHS 33B, of the Orange-Red Group, with a white nectariferous groove surrounded by a bright orange halo blending into a bright red color, RHS 34A, in the center of the petal and blending into a pale orange on the top of the petal. The entire petal area, excluding one inch of the tip, is covered with at least 100 dark, prominent 'pepper spots'. Under side — slightly pubescent with a midrid of pale orange color, RHS 25C, fading into a deeper orange color, RHS 25B, on the outer edges. It should be noted that the flower color may vary either lighter or darker according to the soil and climate in which the plant is grown.

*Texture.*—Leathery.

*Aspect.*—Velvety.

*Papillae.*—Present on the petals and from 4 to 8 in number.

Discoloration: The color tends to fade somewhat as the bloom matures.

Effect of weather: Generally the flower is not affected by wet weather, but ages as the temperature rises.

Persistence: The flower tends to hang on and dry.

Fragrance: None.

Lasting quality:

*On the plant.*—2 to 4 weeks.

*As a cut flower or pot.*—10 days to 2 weeks.

REPRODUCTIVE ORGANS

Stamens:

*Anthers.*—Six in number. Arrangement: orderly around the pistil. Length: about $\frac{1}{4}$ inch. Color: pale orange.

*Filaments.*—About $2\frac{1}{2}$ to 3 inches long.

Pistils:

*Number.*—One.

*Style.*—About 2 inches long.

*Stigma.*—Pale orange in color.

Ovary: Classified as a schizocarp, about $1\frac{1}{2}$ to 2 inches long and 1 inch in diameter, dehiscing into thirds and containing 6 rows of seeds of the usual shape.

This plant has been noted to have an extremely quick and consistently high quality of forcing for cut flower production and as a pot plant, the strong growth habit being of substantial advantage in this regard.

I claim:

1. A new and distinct variety of Asiatic hybrid lily, substantially as herein shown and described, characterized by the form and color of its bright orange-red and speckled flowers, by its relatively short and stocky growth habit, and by its extremely quick and consistently high quality of forcing for cut flower and pot plant production.

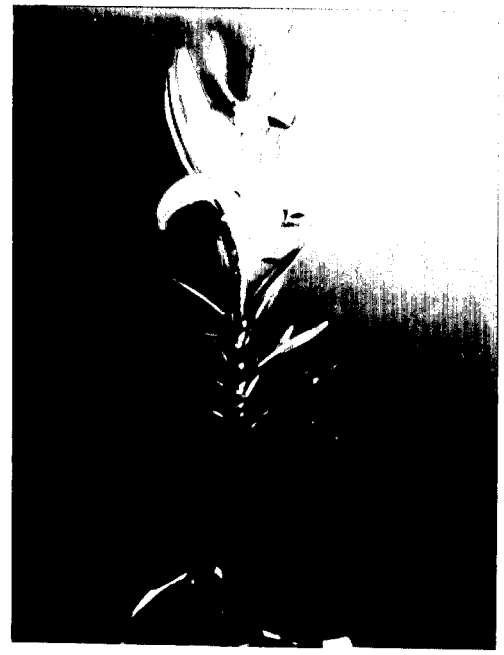
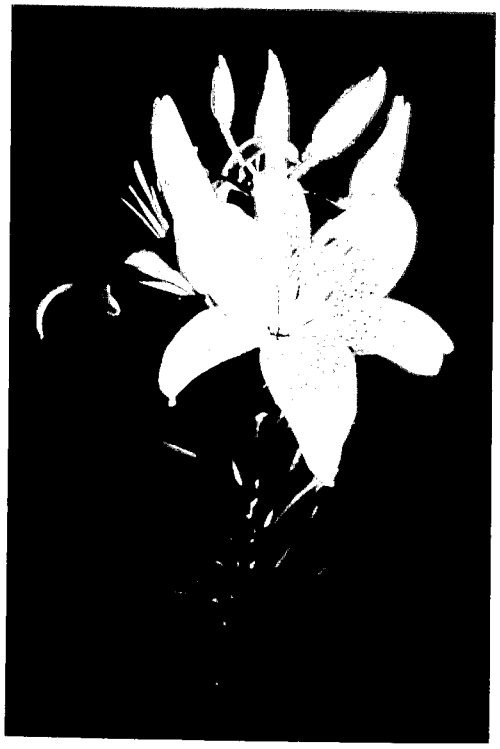

* * * * *